(12) United States Patent
Stambeck et al.

(10) Patent No.: US 11,701,030 B2
(45) Date of Patent: *Jul. 18, 2023

(54) METHOD FOR COLLECTING PARTICLES FROM EXHALED BREATH USING A PORTABLE SAMPLING DEVICE

(71) Applicant: Munkplast AB, Uppsala (SE)

(72) Inventors: Peter Stambeck, Björklinge (SE); Kjell Alving, Uppsala (SE)

(73) Assignee: MUNKPLAST AB, Uppsala (SE)

( * ) Notice: Subject to any disclaimer, the term of this patent is extended or adjusted under 35 U.S.C. 154(b) by 643 days.

This patent is subject to a terminal disclaimer.

(21) Appl. No.: 16/811,162

(22) Filed: Mar. 6, 2020

(65) Prior Publication Data

US 2020/0268280 A1  Aug. 27, 2020

Related U.S. Application Data

(63) Continuation-in-part of application No. 15/986,883, filed on May 23, 2018, now Pat. No. 11,317,827.
(Continued)

(30) Foreign Application Priority Data

Jul. 1, 2015  (SE) .................................... 1550930-0
Nov. 24, 2015 (SE) .................................... 1551526-5

(51) Int. Cl.
*A61B 5/097* (2006.01)
*A61B 5/08* (2006.01)
(Continued)

(52) U.S. Cl.
CPC .............. *A61B 5/097* (2013.01); *A61B 5/082* (2013.01); *A61B 5/091* (2013.01); *A61B 5/742* (2013.01);
(Continued)

(58) Field of Classification Search
CPC . A61B 5/097; A61B 2010/0087; A61B 5/082; A61B 5/091; A61B 2560/0285;
(Continued)

(56) References Cited

U.S. PATENT DOCUMENTS 5,193,551 A * 3/1993 Pilipski ................ G01N 33/497
                                                    73/1.05
10,980,475 B2 * 4/2021 Johnson ............... A61B 5/0836
(Continued)

*Primary Examiner* — Jacqueline Cheng
*Assistant Examiner* — Tho Q Tran
(74) *Attorney, Agent, or Firm* — Reising Ethington P.C.

(57) ABSTRACT

A portable handheld sampling device for collecting aerosol particles in a stream of exhaled breath provided with an inlet and an outlet, wherein the sampling device further comprises a housing and a collecting device holder removably arranged at least partially inside the housing, wherein the housing and the collecting device holder are arranged to guide the stream of exhaled breath through the device from the inlet to the outlet, wherein said collecting device holder comprises at least two cylindrical conduits arranged in parallel, each defining a flow path in fluid connection with the inlet, wherein a cylindrical collecting device is arranged in each conduit, the collecting device being adapted to collect the aerosol particles in the exhaled breath. A method for collecting aerosol particles in exhaled breath of a user using a portable handheld sampling device by means of a reopening breathing maneuver.

17 Claims, 9 Drawing Sheets

Figure 1:
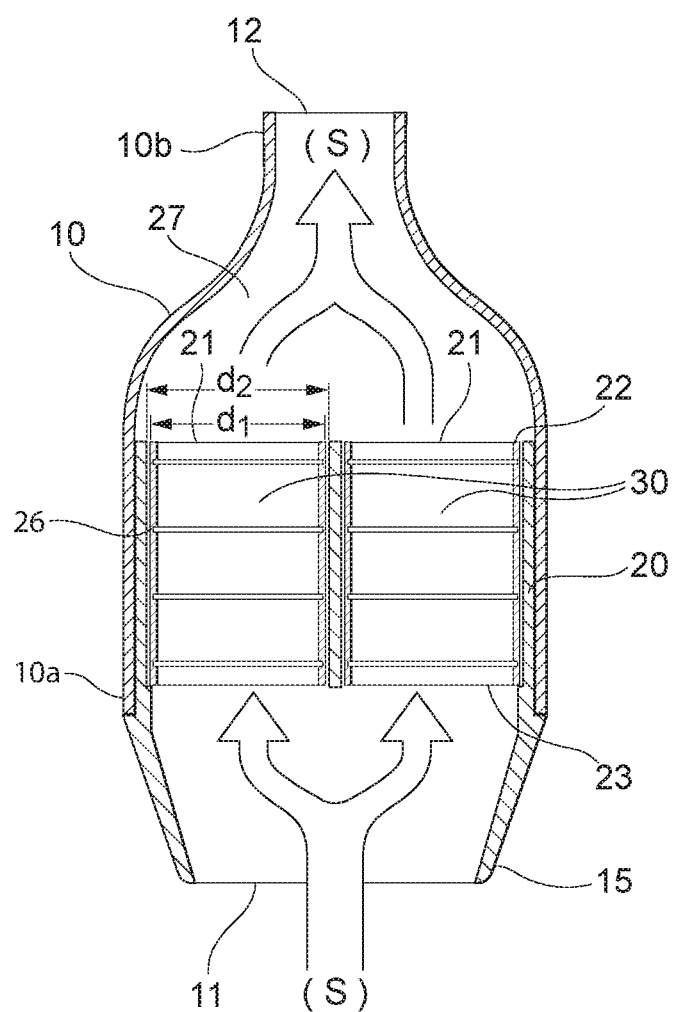

Related U.S. Application Data which is a continuation of application No. PCT/SE2016/051159, filed on Nov. 23, 2016, said application No. 16/811,162 is a continuation-in-part of application No. 15/856,090, filed on Dec. 28, 2017, now Pat. No. 10,898,108, which is a continuation of application No. PCT/EP2016/064110, filed on Jun. 19, 2016.

(51) Int. Cl.
| | | |
|---|---|---|
| *G01N 33/497* | (2006.01) | |
| *A61B 5/00* | (2006.01) | |
| *A61B 5/091* | (2006.01) | |
| *A61B 90/00* | (2016.01) | |
| *A61B 10/00* | (2006.01) | |
| *G01N 1/22* | (2006.01) | |

(52) U.S. Cl.
CPC ............ *A61B 5/7405* (2013.01); *A61B 10/00* (2013.01); *A61B 90/03* (2016.02); *G01N 1/2247* (2013.01); *G01N 33/497* (2013.01); *A61B 2010/0087* (2013.01); *A61B 2560/0285* (2013.01); *A61B 2560/0431* (2013.01); *G01N 2001/2223* (2013.01); *G01N 2001/2244* (2013.01)

(58) Field of Classification Search
CPC ......... A61B 2560/0431; G01N 1/2247; G01N 33/497; G01N 2001/2223; G01N 2001/2244
See application file for complete search history.

(56) References Cited

U.S. PATENT DOCUMENTS

| | | | |
|---|---|---|---|
| 2008/0056946 A1* | 3/2008 | Ahmad | G01N 33/64 422/68.1 |
| 2016/0066817 A1* | 3/2016 | Hannes | A61B 5/097 600/538 |
| 2018/0146886 A1* | 5/2018 | Leard | A61B 5/097 |
| 2020/0187828 A1* | 6/2020 | Wheeler | G01N 33/0011 |

* cited by examiner

Fig. 3
Fig. 4
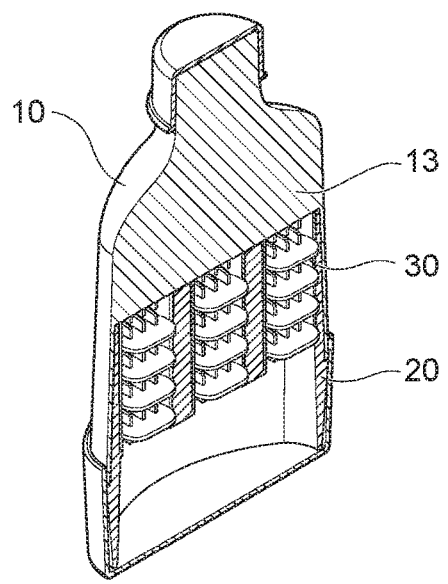
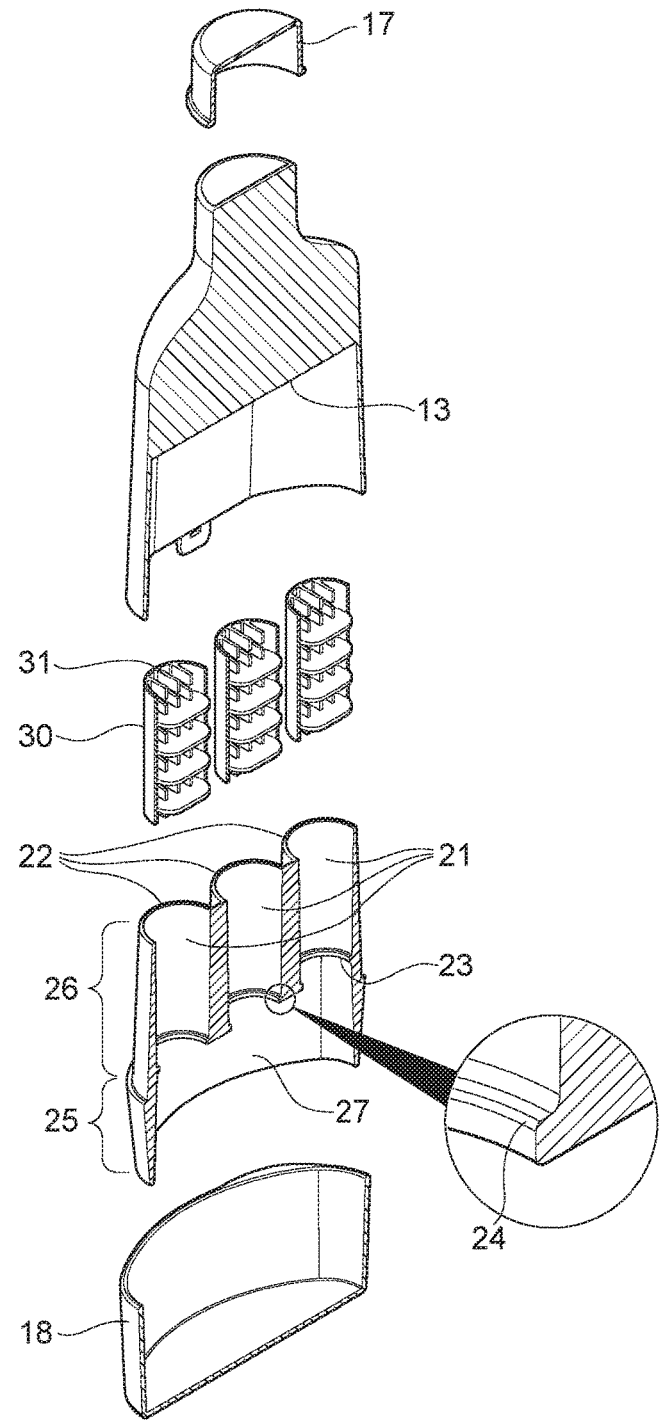

Exhale

Hold your breath

Inhale

Exhale

METHOD FOR COLLECTING PARTICLES FROM EXHALED BREATH USING A PORTABLE SAMPLING DEVICE

CROSS-REFERENCE TO RELATED APPLICATIONS

This application is a continuation-in-part of U.S. non-provisional application Ser. No. 15/986,883, titled "Portable Sampling Device, Stand and Method for Collecting Particles from Exhaled Breath" and filed on May 23, 2018, which is a continuation of International Application No. PCT/SE2016/051159, filed 23 Nov. 2016, which claims the benefit of Swedish Patent Application No. SE 1551526-5, filed 24 Nov. 2015. This application is also a continuation-in-part of U.S. non-provisional application Ser. No. 15/856,090, titled "A device for collecting particles in an exhaled air flow" and filed on Dec. 28, 2017, which is a continuation of International Application No. PCT/EP2016/064110, filed 19 Jun. 2016, which claims the benefit of Swedish Patent Application No. SE 1550930-0, filed 1 Jul. 2015. The entire contents of all the above-mentioned applications are hereby incorporated by reference.

TECHNICAL FIELD

The present invention relates generally to a portable handheld sampling device for collecting particles in a flow of exhaled breath from a user, a stand for such a portable sampling device and a method for collecting particles in a flow of exhaled breath from a user using such a device. Said particles may be aerosol particles formed or found in the alveoli of the lungs, such as biomarkers or exogenous compounds containing traces of drugs or other substances.

BACKGROUND ART

Human breath contains aerosol particles that are formed from the respiratory tract lining fluid covering the airways during normal breathing. Said particles have a size of between 0.1 and 2 μm, with an average size of between 0.3 and 0.8 μm. See article Schwarz et al. (2010). "Characterization of Exhaled particles from the Healthy Human Lung". *Journal of aerosol medicine and pulmonary drug delivery*, 23(6). The aerosol particles carry non-volatile components containing diagnostic information or biomarkers and are often studied as the breath condensate fraction. In this aerosol fraction, both lipids and peptides of endogenous origin have been demonstrated. It has also been discovered that exogenous compounds are present in the exhaled breath. Such exogenous compounds may for example be drugs and narcotics. The respiratory tract lining fluid contains large quantities of antioxidants and surfactant. The surfactant phase is lipophilic and may represent a compartment for the exogenous compounds. Thus, exhaled breath can be used as a matrix for several types of testing such as for example testing of a medical condition or a medical treatment procedure, abused drug testing or doping testing. It can also be used for medical research.

The major component of lung surfactant is the phospholipid dipalmitoylphosphatidylcholine (DPPC). DPPC is primarily produced by alveolar type II pneumocytes, cells that reside in the pulmonary alveolar wall. Another PC found in the airways, palmitoyl-oleoyl-PC (POPC), is a common component in cell membranes, and seems to be more uniformly distributed throughout the respiratory tract. Collecting non-volatile material from exhaled breath has previously shown a DPPC/POPC ratio of about 4, indicating a peripheral origin of the collected material (Larsson P et al. (2017), "The effect of exhalation flow on endogenous particle emission and phospholipid composition", *Respiratory Physiology & Neurobiology*, 243: 39-46). A large and complicated instrument was used to collect particles through impaction, as disclosed in WO 2009/045163.

The peripheral (small) airways and alveoli are in close contact with the blood circulation. For example, the lungs are pharmacologically active organs and affect the blood concentrations of intravenously administered drugs. Through the pulmonary circulation, the lungs can take up, retain, metabolize and delay the release of many drugs and compounds. The chemicals and drugs that are taken up by the lungs may have diverse chemical structures and pharmacological activities. Furthermore, the bronchial circulation nourishes the bronchial tree all the way down to and including the terminal bronchioles, and blood plasma is actively exuded in a controlled manner from the bronchial circulation to the airway lumen, both in health and disease. This results in the abundance of serum albumin in non-volatile material collected from exhaled breath, as previously reported in the article referenced above.

With the discovery of exogenous aerosol particles present in exhaled breath, a need for new methods and devices for collecting and analyzing said aerosol particles in exhaled breath has arisen. For accurate analysis, it is of importance that as many of the aerosol particles as possible are collected from a sample breath. Further, in some applications, such as for example testing for drug abuse or doping, the collection of particles is performed away from a lab environment. However, there is a lack of methods and devices for easy collection of said aerosol particles in exhaled breath.

It is also previously known to collect aerosol particles in exhaled breath using different types of filters. In an article published in the *Journal of Pharm Biomed Anal*. 2011 Dec. 15; 56(5):1024-8. doi: 10.1016/j.jpba.2011.08.004 (Epub 2011 Aug. 9) with title "Demonstration that methadone is being present in the exhaled breath aerosol fraction", two types of filters are tested when collecting aerosol particles for analysis of methadone in exhaled breath. Said two types of filters were a glass fiber filter and a polymer filter which where compared with an earlier used C18 silica filter. The polymer filter collected more than 90% of the aerosol particles in the exhaled breath. The polymer filter also has the practical advantage of having a low flow resistance making it possible to sample without pumping assistance. However, extracting the collected particles from a polymer filter is a complex process requiring a large amount of extraction fluid to separate the particles from the filter fibers.

WO 2012/120140 discloses a portable sampling device for collecting a sample from exhaled breath of a subject, the sampling device comprising a housing having at least one inlet and at least one outlet for the exhaled breath to exit through, and a sampling membrane arranged in the housing to collect aerosols from the exhaled breath. After a sample has been collected, the sampling membrane is removed from the housing and the collected aerosols and particles are extracted by immersing the sampling membrane in a suitable solvent. The removal of the sampling membrane is cumbersome and requires handling which may contaminate the sample, due to the flexible nature of the synthetic filter fibers and the way the sampling membrane is fastened to the housing (melted edge, separate support structure etc.).

Thus, there is a need to improve the prior art devices for collecting biomarkers, surfactant and other particles in exhaled air. Particularly, there is a need to provide sampling devices and methods which facilitate handling of the collected aerosol samples and reduce the risk of contamination.

SUMMARY OF INVENTION

The present invention provides methods and devices for collecting aerosol particles in exhaled breath to overcome the problems encountered by the available prior art as outlined above. In a first aspect of the present invention, there is provided a portable handheld sampling device for collecting particles in a stream of exhaled breath provided with an inlet and an outlet. The sampling device comprises a housing and a collecting device holder removably arranged at least partially inside the housing, wherein the housing and collecting device holder are arranged to guide the stream of exhaled breath through the device from the inlet to the outlet. Said collecting device holder comprising at least two cylindrical conduits arranged in parallel, each defining a flow path in fluid connection with the inlet, wherein a collecting device is arranged in each conduit, the collecting device being adapted to collect the aerosol particles in the exhaled breath.

The present invention provides a compact and simple sampling device which is easy to use, increases the amount of aerosol particles collected from exhaled breath and allows for simultaneous collection of two or more samples under identical testing conditions.

In a preferred embodiment, the collecting device is movably arranged in the collecting device holder such that the collecting device may be removed from the collecting device holder only when the collecting device holder is separated from the housing. Further, the collecting device may have a diameter smaller than the flow path diameter. By providing a collecting device movably arranged in a flow path of the collecting device holder, the present invention facilitates handling of the collecting device, once the sample from the exhaled breath of the user has been collected. In the context of the present invention, the term "movably arranged" should be interpreted such that the collecting device is free to move with respect to the holder, e.g. by the effect of gravity. Medical personnel conducting the sampling procedure need not handle the collecting device directly with their hands, since the collecting device is easily removable from the collecting device holder by the effect of gravity. It is also conceived within the scope of the invention that the diameter of the collecting device is selected to obtain a snug fit with the conduit of the collecting device holder such that the collecting device is retained in the conduit even under the effect of gravity.

In a preferred embodiment, the collecting device is movably arranged in a direction parallel to the flow path in the collecting device holder. This design allows for simple construction and optimal flow of exhaled breath through the collecting device in the flow path to further increase the amount of collected particles in the sampling device.

By providing at least two, preferably at least three, separate flow paths with each having a collecting device movably arranged therein, it is possible to take several samples from one exhaled breath of the user under identical conditions. This allows for multiple opportunities for analyzing identical samples, for example at different times, or by different laboratories for verifying the analysis results. When three flow paths are provided one sample may be analyzed at present, one sample is a reference and the third sample may be stored for future reference.

In an alternative embodiment, the portable sampling device further comprises means for retaining the collecting device in an upstream direction in the flow path of the collecting device holder. The flow path has a cylindrical shape and the retaining means comprises an inwardly directed flange at a proximal end of the flow path. By providing retaining means, in the shape of an inwardly directed flange at a proximal end of the flow path, the collecting device is held in place in the collecting device holder during assembly.

In a further preferred embodiment, the housing comprises an abutment member adapted to abut against a distal end of the collecting device when the collecting device holder is arranged inside the housing. The abutment member of the housing works together with the retaining flange in the flow path of the collecting device holder to fix the collecting device in position in the flow path when the portable sampling device is assembled. This ensures that the collecting device remains in place during sampling.

In an advantageous embodiment, the portable sampling device further comprises corresponding locking means arranged on the housing and the collecting device holder, respectively. Preferably, the locking means comprises a cantilever snap-fit connection including at least one deflectable tab comprising a recess arranged on the housing and at least one cantilevered protrusion arranged on the collecting device holder, wherein the at least one protrusion is adapted to mate with and engage the recess in the at least one deflectable tab when the housing and the collecting device holder are brought together. By providing locking means, e.g. in the form of a snap-fit connection, a fast and secure attachment of the housing and the collecting device holder is achieved which ensures that any manipulation of or tampering with the sampling device is immediately noticed during any step of taking and preparing a sample from an exhaled breath of a user. Thus, it can be ensured that the sampling device remains intact during the entire process from manufacture and assembly to collecting a sample and analyzing the sample.

In a preferred embodiment, the portable sampling device further comprises at least one lid to cover the inlet and/or the outlet of the sampling device. The lid(s) prevent contamination of the interior of the sampling device before and after use. Preferably, the at least one lid comprises at least one outwardly directed flange for easy removal.

In a preferred embodiment, the sampling device further comprises a device arranged to measure volume and/or flow of exhaled breath connected in fluid communication with the outlet. For instance, a balloon with an aperture therein or a spirometer may be used to measure the volume and/or flow of expired air from the lungs of the user and thereby provide an indication that a sufficient sample of exhaled breath has been provided.

In an alternative embodiment, the portable sampling device is disposable. To this end, the sampling device is made from an inexpensive, medically acceptable material such as plastic, preferably polypropylene (PP), polyvinylidene fluoride (PVDF), fluorinated ethylene propylene (FEP) and/or polytetrafluoroethylene (PTFE). The material is chosen to minimize or eliminate any reaction or interaction between the collected aerosol particles and the sampling device.

In a second aspect of the present invention, there is provided a method for collecting aerosol particles of a user using a portable handheld sampling device for collecting aerosol particles in a stream of exhaled breath provided with an inlet and an outlet, wherein the sampling device further comprises a housing and a collecting device holder removably arranged at least partially inside the housing, wherein the housing and the collecting device holder are arranged to guide the stream of exhaled breath through the device from the inlet to the outlet, wherein said collecting device holder comprises at least two cylindrical conduits arranged in parallel, each defining a flow path in fluid connection with the inlet, wherein a cylindrical collecting device is arranged in each conduit, the collecting device being adapted to collect the aerosol particles in the exhaled breath, the method comprising the following steps to be performed by the user:

exhaling deeply to residual volume;
holding breath during a first predetermined period of time;
inhaling deeply to total lung capacity;
placing the portable handheld sampling device at the mouth of the user; and
exhaling through the portable handheld sampling device from total lung capacity to residual volume during a second predetermined period of time.

During emptying of the lungs of air, that is exhaling to residual volume (RV), the smallest airways (non-cartilaginous terminal bronchioles, respiratory bronchioles, alveolar ducts, and alveolar sacs) will collapse, especially during a short breath hold at residual volume. When inhaling again, these airways reopen, causing a rupture of the superficial epithelial fluid layer leading to an increased particle formation. By collecting exhaled material using the portable handheld sampling device mentioned above, this breathing maneuver has been shown to increase the exhaled particle mass of DPPC per volume of air approximately 10 times compared to a normal exhalation procedure with prior inhalation from functional residual capacity. With the sampling device and breathing maneuver according to the present invention, a DPPC/POPC ratio of approximately 4.5 in healthy volunteers has also been shown, supporting that the collected material has a peripheral airway origin.

In a preferred embodiment, the steps to be performed by the user are displayed on a displaying device. By displaying the method steps on e.g. a smartphone, tablet or computer, the user may be assisted in carrying out the breathing maneuver in a correct manner to ensure that a maximum amount of aerosol particles, such as DPPC emanating from the peripheral airways, are exhaled and collected by the portable handheld sampling device. In one embodiment, the visualization of the method steps may be in the form of written, audible and/or graphical instructions or a combination thereof. Preferably, a timer is displayed on the displaying device to indicate the first and/or second predetermined time to further facilitate for the user to follow the correct breathing maneuver.

In an alternative embodiment, the method further comprises connecting a device arranged to measure volume and/or flow of exhaled breath in fluid communication with the outlet of the sampling device prior to the user exhaling through the sampling device. For instance, a balloon with an aperture therein or a spirometer may be used to measure the volume and/or flow of expired air from the lungs of the user and thereby provide an indication that a sufficient sample of exhaled breath has been provided by the user.

BRIEF DESCRIPTION OF DRAWINGS

The invention is now described, by way of example, with reference to the accompanying drawings, in which:

FIG. 1 shows a perspective view of a portable handheld sampling device according to a first embodiment of the invention according to the first aspect in an assembled and operable state;

FIG. 2 shows an exploded view of a sampling device according to a second embodiment of the invention according to the first aspect, wherein the individual components are illustrated in a disassembled state;

FIG. 3 shows a cross-sectional view of the assembled sampling device according to the second embodiment of the invention according to the first aspect;

FIG. 4 shows a cross-sectional view of the disassembled sampling device in FIG. 2;

FIGS. 5*a* and 5*b* show details of the sampling device in non-assembled and assembled operative mode, i.e. without closures at the inlet and outlet;

FIG. 6 shows a cross-sectional view taken along the cut A-A of a sampling device according to a modified second embodiment of the invention according to the first aspect;

FIG. 7 shows a bottom view of FIG. 6.

FIG. 8 shows a perspective view of a stand for a portable handheld sampling device;

FIGS. 9*a*-9*c* show different steps employed in a method;

FIG. 10 shows a cut-away portion of the stand illustrating disassembly of the portable sampling device;

FIG. 11 shows a tool for handling a collecting device;

FIGS. 12*a* and 12*b* show the tool in FIG. 11 in use;

FIGS. 13*a-e* show a user performing different steps of a method for collecting aerosol particles in exhaled breath using a portable handheld sampling device; and FIG. 14 shows a graph of lung volume vs. time during the sequence of steps shown in FIGS. 13*a-e*.

DETAILED DESCRIPTION OF EMBODIMENTS

In the following, a detailed description of a portable handheld sampling device, a sampling device stand and a gripping tool is presented. Additionally, a method for collecting aerosol particles in exhaled breath using a portable handheld sampling device. In the drawing figures, like reference numerals designate identical or corresponding elements throughout the several figures. It will be appreciated that these figures are for illustration only and are not in any way restricting the scope of the invention.

FIG. 1 shows in a perspective view a portable sampling device 1 according to a first embodiment the present invention in an assembled but operable state. FIG. 2 shows a portable sampling device 1 according to a second embodiment of the invention in an exploded view of the components of the sampling device 1. Furthermore, FIGS. 3 and 4 show cross-sectional views of the sampling device according to the second embodiment in FIG. 2 taken along a longitudinal axis of the sampling device in the direction of flow of exhaled breath. In the context of the present invention, the term 'portable sampling device' shall be interpreted as referring to a stand-alone, handheld device which is dimensioned to be carried and used by hand by a user. The sampling device 1 is adapted to be used for collecting particles in a stream of exhaled breath, as outlined above.

The sampling device 1 comprises an inlet 11 at a first, proximal end and an outlet 12 at a second, distal end. The terms proximal and distal when referring to the sampling device 1 should be interpreted as indicating the portion closest to and furthest away from the user, respectively, when blowing into the sampling device 1. Other terms may be used herein to describe different portions of the sampling device 1, such as upstream and downstream, which relate to the direction of flow (S) of the exhaled breath when the user blows into the sampling device 1. The terms upper and lower side of the sampling device 1 may also be used. The terms upper and lower side of the sampling device relate to the sides located closest to the nose or chin, respectively, when the inlet 11 is located in the user's mouth during the sampling procedure. The inlet 11 is formed as a mouthpiece arranged to receive the exhaled breath from the user and directing towards the outlet 12. The mouthpiece may in one embodiment have an oval shape in order to better fit into the mouth of the user. The sampling device further comprises an outer or external housing 10 comprising a first, proximal and a second, distal housing end 10a, 10b. The outlet 12 is arranged in said second, distal housing end 10b.

In order to collect the particles in the exhaled breath, the sampling device 1 further comprises at least one collecting device 30, movably arranged in a collecting device holder 20, which in turn is removably arranged at least partially inside the housing 10. The first, proximal housing end 10a of the housing 10 is adapted to receive the holder 20 to ensure a substantially airtight fit between the housing 10 and the holder 20, i.e. there is substantially no gap between the internal wall of the housing 10 and the external surface of the holder 20 such that substantially no part of the exhaled breath may pass there between. At least a proximal or upstream portion 25 of the holder 20 may remain outside the housing 10 when the sampling device 1 is assembled. The proximal portion 25 may have a greater width and/or thickness than the remaining distal or downstream portion 26 of the holder 20, such that the outer surface of the housing 10 is flush with the outer surface of the proximal portion 25.

In the distal portion 26 of the holder 20 there are provided at least two flow paths 21, in which the collecting device 30 is seated, in fluid connection with the inlet 11 to guide the stream of exhaled breath from the inlet 11 of the housing 10 through the holder 20 and the collecting device 30. The flow paths 21 may be of substantially cylindrical shape with a diameter d2, and the collecting device 30 may be in the form of a cylinder with a diameter d1, e.g. as disclosed in U.S. non-provisional application Ser. No. 15/856,090, which is hereby incorporated by reference in its entirety. The collecting device 30 hereby replaces the membrane filter used in the prior art and is adapted to collect aerosol particles, preferably aerosol particles consisting mainly of surfactant functioning as biomarkers, in exhaled breath. The collection device comprises at least four partition walls, arranged at a distance from each other and extending in a direction essentially perpendicular to the cylinder walls, partly covering the inner cross section of the collecting device. The aerosol particles are accumulated on said walls when the flow of exhaled breath interacts with the walls when passing thorough the collecting devices 30 on its way from the inlet 11 to the outlet 12. Other shapes of the collecting device 30 may also be considered, as long as they can be movably arranged in the flow paths 21 to ensure easy removal without requiring extensive handling. The diameter d2 of the flow paths 21 is substantially smaller than the cross-sectional area of the holder 20 and of the housing 10. The remaining portion of the cross-sectional area of the holder 20 is formed with a wall, perpendicular to the flow path and direction of flow of exhaled breath through the sampling device 1 to prevent flow outside the flow paths 21. This decreased diameter of the flow paths 21 compared to the cross-sectional area of the housing 10 leads to an increased velocity of the flow of exhaled breath through the flow paths 21 and increased turbulence when passing through the collecting device 30, which is advantageous for the collection of aerosol particles in the exhaled breath. Another advantage is that it also allows for arrangement of more than two flow paths 21 in the holder 20.

To ensure that the collecting device 30 is movably arranged in the flow path 21, the collecting device 30 has a diameter d1 which is smaller than the diameter d2 of the flow path 21, yet sufficiently big to minimize the gap between the outer surface of the collecting device 30 and the wall of the flow path 21 such that a major part, if not all, of the exhaled breath passes through the collecting device 30.

As may be seen in FIG. 1, which shows the assembled sampling device 1 in a cross-sectional view, the flow path 21 is arranged in a direction parallel to the direction of flow S of the exhaled breath through the sampling device 1. Further, the collecting device 30 is movably arranged in the direction of the flow path 21 such that the collecting device 30 may only be moved in relation to the holder 20 in this direction. This configuration allows for facilitated handling of the collecting device 30 once the particle sample from the exhaled breath has been collected. The operator can easily remove the collecting device 30 from the sampling device 1 by disassembling the holder 20 from the housing 10 and turning the holder 20 on end to let the collecting device 30 slide out by the force of gravity. In other embodiments, the diameter d1 of the collecting device 30 is selected to provide a snug fit with the conduit of the flow path 21 such that the collecting device 30 remains lodged in the collecting device holder 20 until actively removed therefrom, e.g. by means of a suitable tool for gripping the collecting device 30.

FIG. 4 shows a close-up view of the collecting device holder 20. As may be seen, the holder 20 has three cylindrical conduits arranged parallel and side-by-side, each defining a flow path 21. Having two or more parallel flow paths 21 is an advantage compared to known sampling devices, since it allows for simultaneous taking of multiple samples under identical conditions. Thus, one sample may be analyzed at present and the other samples may be stored for future reference.

The flow paths 21 culminate or debouch into a common space 27 in the housing 10. The upstream or proximal end 23 of each flow path 21 has retaining means in the form of an inwardly projecting annular flange 24 to hold the collecting device 30 in place after insertion. In other words, the collecting device 30 is movable in an downstream or distal direction of the holder 20, but may not move past the retaining flange 24. Other means of retaining the collecting device 30 may be foreseen, such as an obstruction in the form of bars, webbing or spokes extending across the flow path 21 perpendicular to the flow direction.

The housing 10 also comprises an abutment member for abutting against the collecting device 30 when the sampling device 1 is assembled. In FIG. 4, the housing 10 is shown in a cross-sectional view wherein an abutment member in the form of a partition 13 is seen extending in the longitudinal direction from the outlet 12 at the distal end of the housing 10. When the sampling device 1 is assembled, as shown in FIG. 3, the partition 13 extends in a proximal direction toward the distal end of the holder 20 and abuts against the distal end 31 of the collecting devices 30 arranged in the flow paths 21. As may be seen, the distal end 31 of each collecting device 30 is arranged flush with the distal end 22 of the flow path 21. It may also be foreseen that the longitudinal extension of the collecting device 30 is greater than that of the flow path 21. The partition 13 may in that case abut only against the distal end 31 of the collecting device. Also, the partition 13 need not extend the whole distance from the outlet 12, as long as it abuts against the collecting device 30. With this configuration, the collecting devices 30 are securely held in place in the assembled sampling device 1, but may easily be removed from the holder 20 when the housing 10 and holder 20 are separated from each other after completion of taking the sample from the exhaled breath. Other means of retaining the collecting device 30 may be foreseen, such as an obstruction in the form of webs or bars extending perpendicular against the flow direction S and abutting against the collecting devices 30.

Figure 5A:
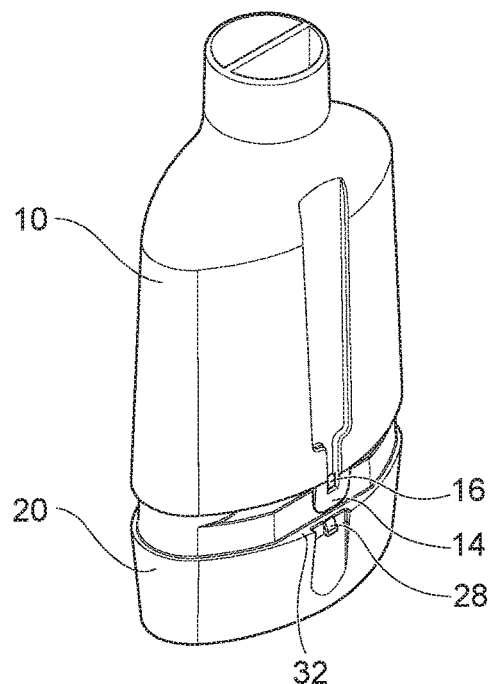
Figure 5B:
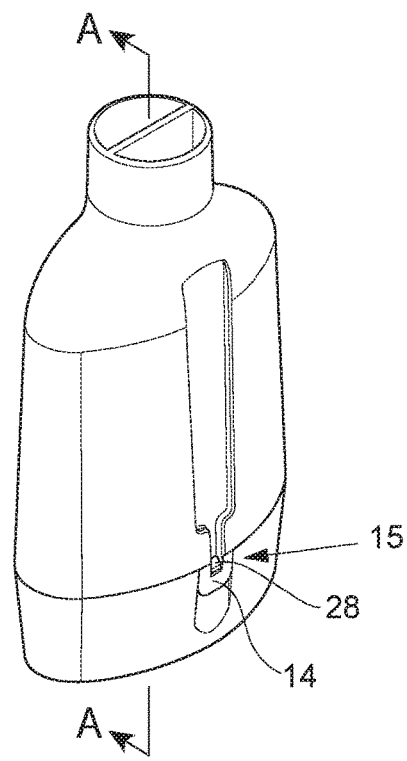

In order to ensure that the portable sampling device 1 has not been manipulated or tampered with, the housing 10 and collecting device holder 20 comprise corresponding complementary locking means which are adapted to be brought into engagement with each other when the housing 10 and holder 20 are assembled together to form the operative mode of the sampling device. One example of a locking means shown in FIGS. 5a and 5b is a cantilever snap-fit connection 15 wherein the housing 10 comprises a deflectable tab 14 including a recess 16 and the holder 20 comprises a cantilevered protrusion 28 configured to mate and engage with the recess 16. During assembly, the holder 20 containing the collecting devices 30 is brought into the housing 10. This causes the protrusion 28 to deflect the tab 14 outwardly until it snaps into a locking position, wherein the protrusion 28 is located in the recess 16, once the housing 10 and holder 20 have been fully assembled. The deflectable tab 14 may be manufactured such that any attempt to bend or tamper with the tab 14 to open the sampling device 1 will cause the tab 14 to bend or break off. Hence, the user and/or the operator will immediately see if the sampling device 1 has been manipulated prior to or during use. Locking means may be arranged on both sides of the housing 10 and holder 20, or only on one side.

Figure 2:
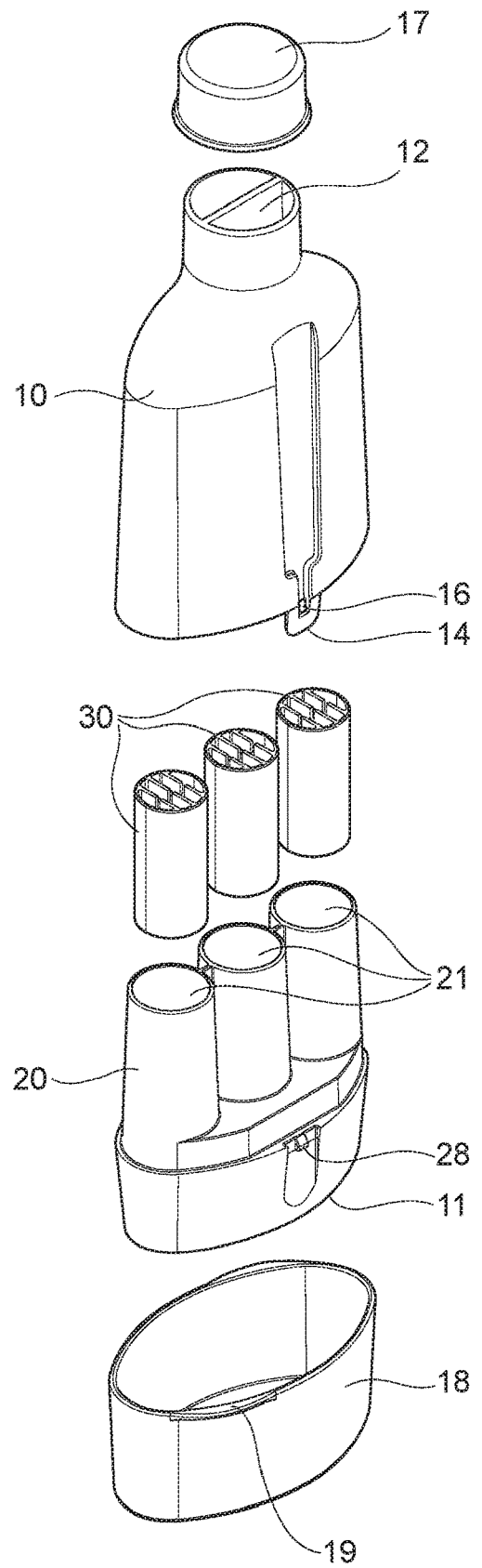

The sampling device 1 further comprises a lid 17 to cover the outlet opening 12 of the housing 10, once a sample has been taken, in order to protect the sample from contamination. A lid 18 for the mouthpiece at the inlet opening 11 of the sampling device 1 may also be provided as shown in FIGS. 1 and 2. The lid 17 has outwardly directed flanges 19 to facilitate removal of the lid 18 from the sampling device.

The portable sampling device 1 according to the present invention is intended to be disposable for one-time use and therefore made from inexpensive, but medically acceptable material, such as plastic. Preferable materials include polypropylene (PP), polyvinylidene fluoride (PVDF), fluorinated ethylene propylene (FEP) and/or polytetrafluoroethylene (PTFE). Other materials such as metal or glass are also within the scope of the present invention.

Figure 6:
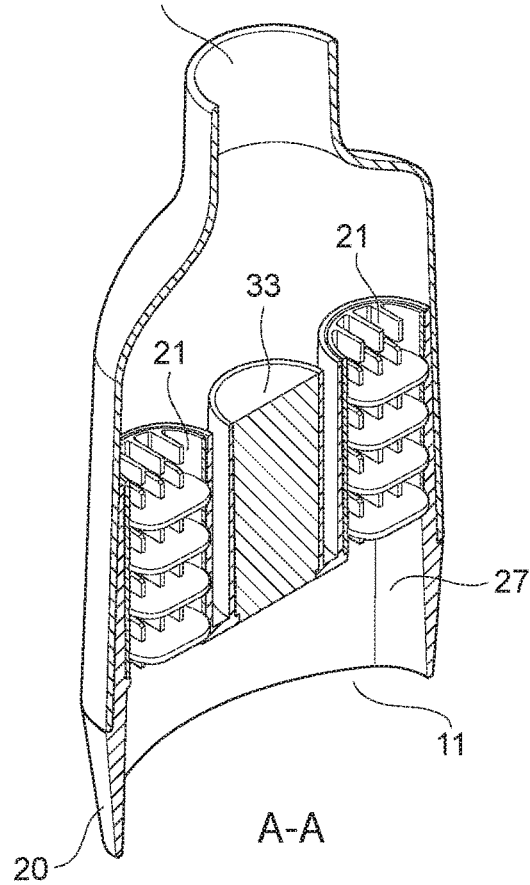

In FIG. 6, there is shown an alternative design of the sampling device according to the first aspect of the invention, i.e. a sampling device comprising at least two flow paths 21 in fluid connection with the inlet 11. Here a holder 20 according to the second aspect, i.e. with three circular openings are used, but the centrally placed opening is closed off by a wall, insert or other type of closure 33. When closing off one of the openings the flow of breath S is divided in to two flow paths instead of three. This may be useful when a user is having difficulty to provide an exhalation through the device with enough flow to fill three collecting devices 30 with the sufficient amount of breath sample.

In one alternative embodiment, a device for measuring or visualizing the amount of breath exhaled through the sampling device is arranged in fluid communication with the outlet 12. Such a device may for example be a flow meter, a spirometer, an inflatable bladder or bag or other devices arranged to visualize a flow. In one embodiment, a balloon with an aperture of about 3-4 mm diameter formed therein may be threaded onto the outlet 12. When an insufficient exhalation rate is detected one of the flow paths may be closed off, for example by a plug in insert as shown in FIG. 6, to facilitate for the user to provide the sufficient flow through the device.

Figure 7:
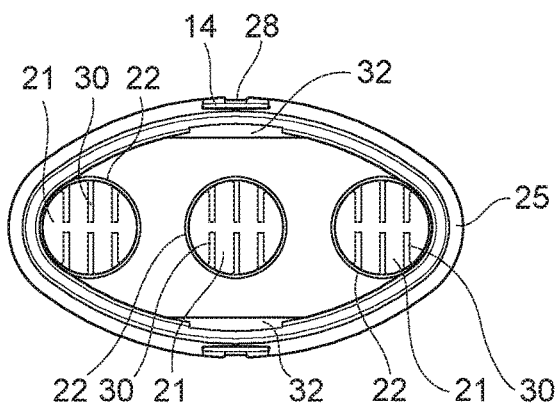

FIG. 7 shows a bottom view of the sampling device in FIG. 6. The housing 10 comprises at least one wall portion 32 protruding essentially perpendicular to the housing outer wall into the common space 27. The at least one wall portion 27 is arranged to protrude into the common space 27 and act as a saliva trap, preventing excessive amount of saliva and other large particle contamination, such as for example food, from entering the collecting devices 30. I.e. when the sampling device is arranged in the user's mouth, the wall portion 32 protrudes into common space 27 from the lower side of the device in order to stop the particles heavier and larger than exhaled air with the sufficient amount of surfactant. If at least two opposite wall portions 27 are used, the device 1 does not have to have a predefined upper and lower side. In the embodiment shown in FIGS. 5a and 7 the wall portion 32 is an integrated part of the housing 20 designed as a step.

Figure 8:
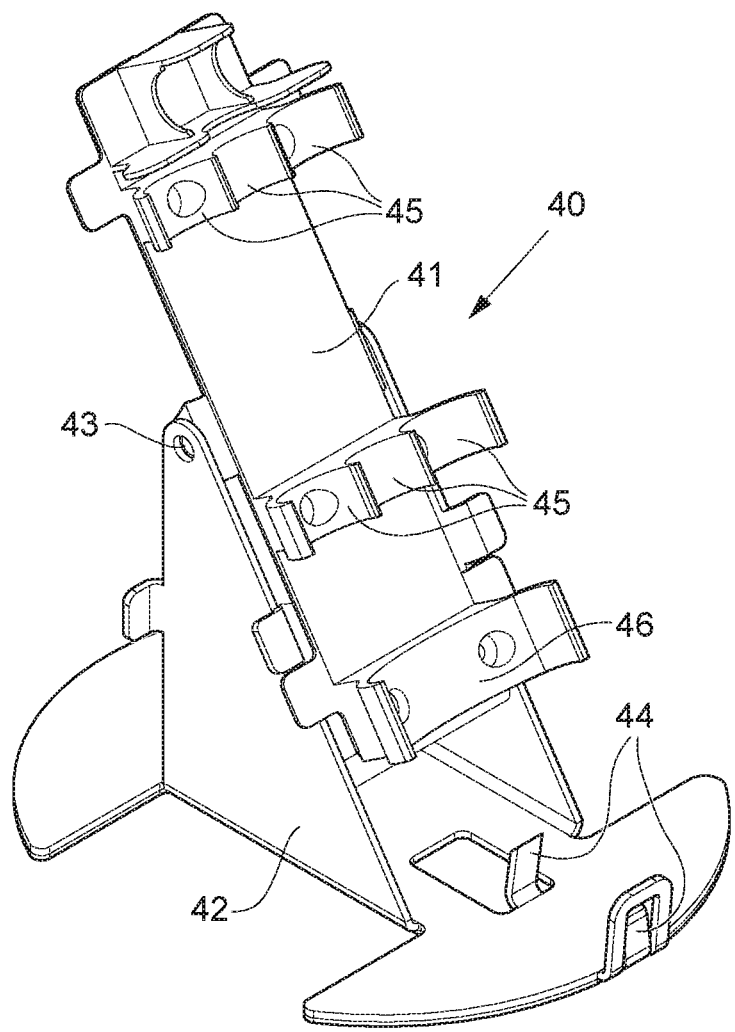
Figure 9A:
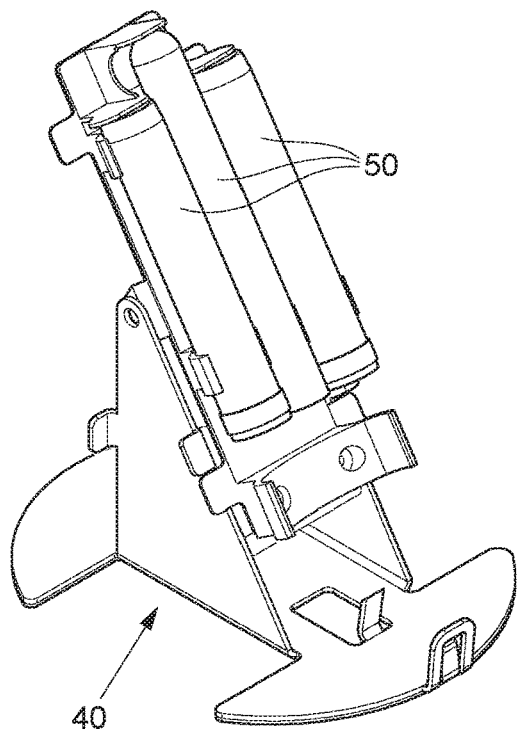

In FIG. 8, there is shown a stand 40 according to a second aspect to be used together with a portable sampling device 1 according to the first aspect. The stand 40 comprises one or more grooves or recesses 45 adapted to hold one or more receptacles 50 for receiving a collecting device 30 carrying a sample of particles from an exhaled breath. The receptacle 50 may be a test tube or any other suitable container of preferably cylindrical shape. In FIG. 9a, three receptacles 50 are shown, a test tube in the middle position and cylindrical collection containers with closable lids (not shown) on either side. Further, the stand 40 comprises a recess 46 adapted to hold the collecting device holder 20 in a configuration such that the receptacles 50 are coaxially aligned with the one or more flow paths 21 of the holder 20.

The stand 40 is made to be movable between a first position and a second position. Advantageously, the portion of the stand 40 holding the receptacles 50, i.e. the rack portion 41, is attached to a base portion 42 via a substantially horizontal axis 43 at a center point located substantially halfway along the longitudinal extension of the rack portion 41. The axis 43 is substantially perpendicular to the longitudinal extension of the rack portion 41 and the rack portion 41 may be tilted in relation to the base portion 42 about the axis 43 to bring the stand 40 from the initial, first position shown in FIG. 9a to the final, second position shown in FIG. 9c.

The purpose of tilting the stand 40 from the first position to the second position is to transfer the collecting devices 30, movably arranged in the holder 20, to the receptacles 50 without requiring direct handling of the collecting devices 30 by the operator. Thus, the risk of contamination or mishandling of the collecting devices 30 is greatly reduced, if not completely eliminated.

Figure 9B:
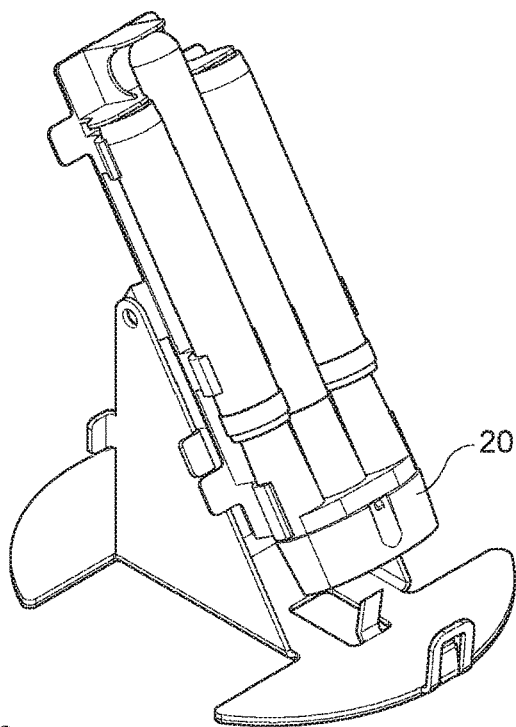
Figure 9C:
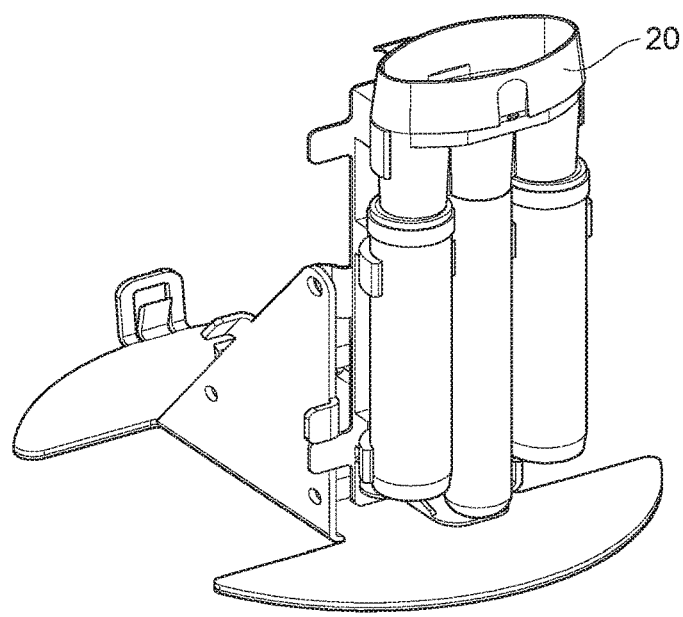

In use, the operator removes the lids 17, 18 and separates the outer housing 10 from the holder 20 containing the collecting devices 30 after a breath sample has been taken. Then, the operator places the required number of receptacles 50 in the stand 40 being in the first position, as shown in FIG. 9a. Next, the holder 20 is placed on the stand 40 such that the inlet openings 22 of each flow path 21 are coaxially aligned with respective openings of the receptacles 50 held in the rack portion 41 of the stand 40, as shown in FIG. 9b. In this first position, the holder 20 is arranged directly below the receptacles 50 and the collecting devices 30 are retained in the flow paths 21 by the inwardly directed flanges 24. Then, the rack portion 41 is tilted with respect to the base portion 42 about the axis 43 to the second position such that the holder 20 and receptacles 50 are turned upside down, with the holder 20 now being arranged directly above the receptacles 50, as shown in FIG. 9c. Since there is nothing retaining the collecting devices 30 at the proximal inlet openings 22 of the flow paths 21, the effect of gravity causes the collecting devices 30 to fall down into the respective receptacles 50.

Figure 10:
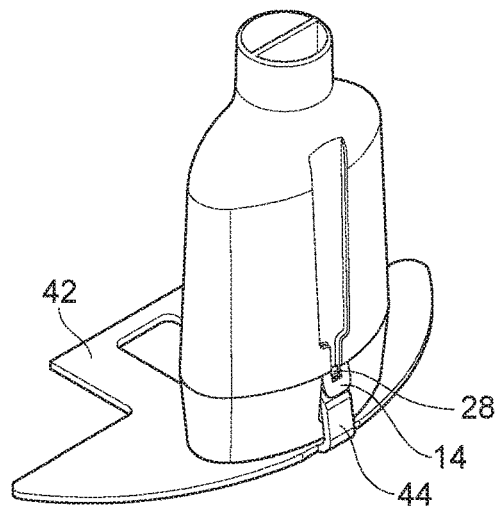

In order to further facilitate handling of the sampling device 1 after a sample has been collected, the base portion 42 of the stand 40 comprises means for separating the housing 10 from the collecting device holder 20, i.e. for opening the locking means holding the housing 10 and holder 20 together. As shown in FIG. 8, the base portion 42 comprises upwardly directed prongs 44 arranged to engage the snap-fit connection 15 on the housing 10 and holder 20. More specifically, the prongs 44 of the base portion 42 are tapered such that when the sampling device 1 is placed on the base portion 42, as shown in FIG. 10, the deflectable tabs 14 of the housing 10 come into contact with the prongs 44 and are pushed outwardly, thereby releasing the engagement with the protrusions 28 of the holder 20. Once the snap-fit connection 15 between the housing 10 and the holder 20 is released, the housing 10 may be lifted off, and the holder 20 may be placed in the rack portion 41 as described above, and shown in FIGS. 9a-c.

After the collecting devices 30 have been transferred to the receptacles 50, an eluent or extraction fluid may be added to the test tube in order to extract the sample particles through the process of elution. The eluent acts as a solvent to wash the sample particles from the walls of the collecting device 30. After adding of the eluent, the test tube is shaken in order to loosen (elute) as many particles as possible from the collecting device 30. Finally the collecting device 30 is removed from the test tube.

Figure 11:
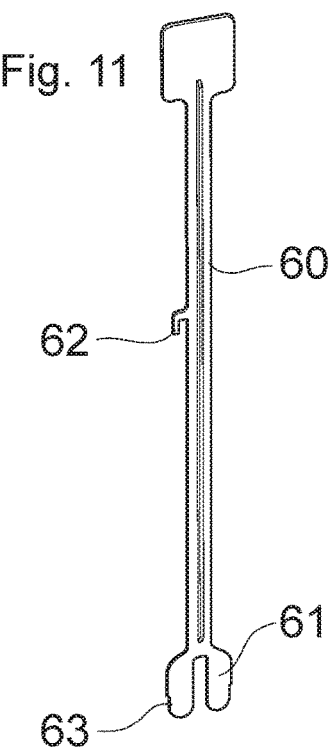
Figure 12A:
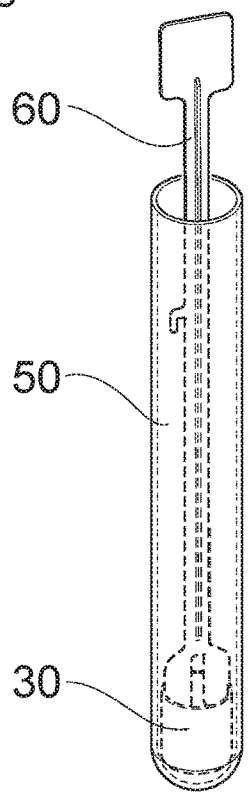

To this end, a tool 60 is provided which is adapted to grip the collecting device 30. The tool 60 is shown in FIG. 11 and comprises gripping means, e.g. in the shape of a fork with resilient tines or prongs 61, arranged on a distal end thereof for engaging one end of the collecting device 30, and means for suspending the tool 60 on a top edge of the test tube. The width of the tines 61 is adapted to the inner diameter of the collecting device 30 such that they are somewhat deflected inwardly when the tool 60 is inserted into the collecting device 30. The resilient nature of the tines 61 is due to the shape and resiliency of the material of the tool 60, preferably a plastic material such as polypropylene (PP), polyvinylidene fluoride (PVDF), fluorinated ethylene propylene (FEP) and/or polytetrafluoroethylene (PTFE). Each tine 61 may have a notch or indentation 63 to provide a stop for the collecting device 30. To remove the collecting device 30 from the receptacle 50, the tool 60 is introduced into the receptacle such that the tines 61 engage and hold the collecting device 30, as shown in FIG. 12a, and both are subsequently withdrawn and discarded together.

Figure 12B:
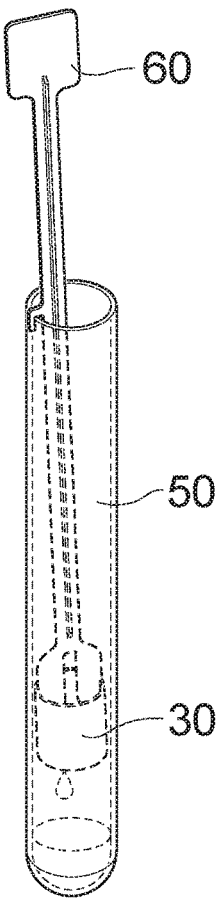

Since the eluent fluid is expensive, it is preferable that most, if not all, of the eluent fluid containing the extracted particles (also called eluate) is recovered. This also ensures that as many of the collected particles as possible are recovered for subsequent analysis. For recovery, the eluate is allowed to drip off the collecting device 30 before discarding the latter. By suspending the gripping tool 60 on the edge of the test tube as shown in FIG. 12b, the operator can leave the collecting device 30 suspended in place for a longer time to allow for the eluate to drip off, without needing to hold the gripping tool 60. In this way, a plurality of collecting devices 30 may be suspended on respective test tubes more or less simultaneously to allow for drip-off of the eluate, thus ensuring efficient handling of the collecting devices 30 and maximizing the amount of eluate.

The suspension means comprises a distally oriented hook 62 arranged at a predetermined distance from the distal gripping means and adapted to engage the top edge of the receptacle 50. The distance between the hook 62 and the gripping means is adapted such that when the gripping tool 60 is suspended on the edge of the test tube, the collecting device 30 is raised above the surface of the eluate in the test tube, as shown in FIG. 12b.

Referring now to FIGS. 13a-e, the different steps in a method for collecting aerosol particles in exhaled breath of a user using the portable handheld sampling device described above in conjunction with FIGS. 1-7 will now be explained. As previously noted, the collecting device 30 as disclosed in U.S. non-provisional application Ser. No. 15/856,090, incorporated herein by reference in its entirety, has been developed to capture aerosol particles such as DPPC from the peripheral airways. The opposing walls which extend over more than half of the diameter of the collecting device 30 and with a spacing smaller than the diameter of the collecting device has been shown to provide an adhesive surface for the aerosol particles which accumulate thereon. On the contrary, larger particles and saliva experience the opposite effect in that they slide off the surfaces of the opposing walls and follow the labyrinth-shaped path to exit the sampling device.

In order to maximize the amount of exhaled aerosol particles collected by the portable handheld sampling device, the present method proposes a breathing maneuver also known as reopening. In a first step shown in FIG. 13a, the user exhales deeply to empty the lungs of air while holding the sampling device away from the mouth. The lung volume will then be close to residual volume (RV), which is the volume of air remaining in the lungs after a maximal exhalation. In the next step shown in FIG. 13b, the user holds their breath during a first predetermined period of time, which may be about 3-5 seconds. As explained above, when the user exhales to residual volume and then holds their breath, the smallest airways (terminal bronchioles) will collapse.

Figure 13A:
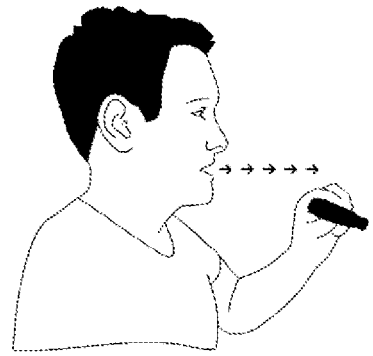
Figure 13B:
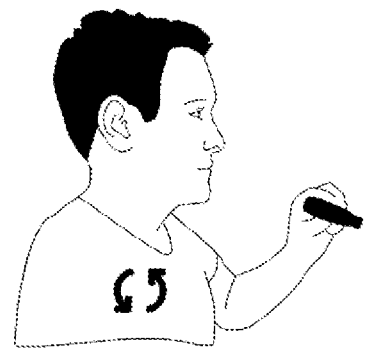
Figure 13C:
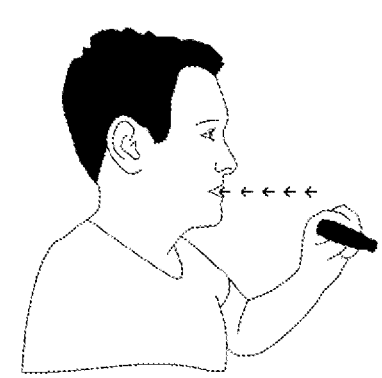

In the next step shown in FIG. 13c, the user inhales deeply to fill the lungs with air. The lung volume will then be at or close to total lung capacity (TLC), which is the volume in the lungs at maximal inflation. Preferably, the inhalation is performed during a period of time which is shorter than the period of holding the breath, e.g. about 2 seconds. When inhaling again, the airways reopen, causing a rupture of the epithelial fluid layer leading to an increased particle formation.

Figure 13D:
Figure 13E:

In the next step shown in FIG. 13d, the user places the portable handheld sampling device to the mouth, closing the lips tightly around the inlet 11 to ensure that all expired air passes through the sampling device. Subsequently, in the final step shown in FIG. 13e, the user exhales slowly through the sampling device from total lung capacity to residual volume during a second predetermined time to allow collection of non-volatile aerosol particles such as DPPC from the peripheral airways by means of the collecting device(s) 30 of the sampling device. Preferably, the exhalation for sampling is performed during a period of time which is longer than the period of holding the breath, e.g. about 6-8 seconds.

Advantageously, the different steps of the breathing maneuver are displayed on a displaying device such as a smartphone or tablet, computer or TV screen to provide a visual aid for the user. In one embodiment, the visualization may be provided by means of an application which may be downloaded on a smartphone, tablet or computer of the user for easy access. The visualization may be in the form of written, audible and/or graphical instructions or a combination thereof. For instance, still and/or moving images similar to FIGS. 13a-e may be displayed on the screen of the smartphone, tablet or computer of the user, accompanied by written and/or audible instructions. Additionally, a timer may be displayed to indicate the duration of the different steps to the user.

Figure 14:
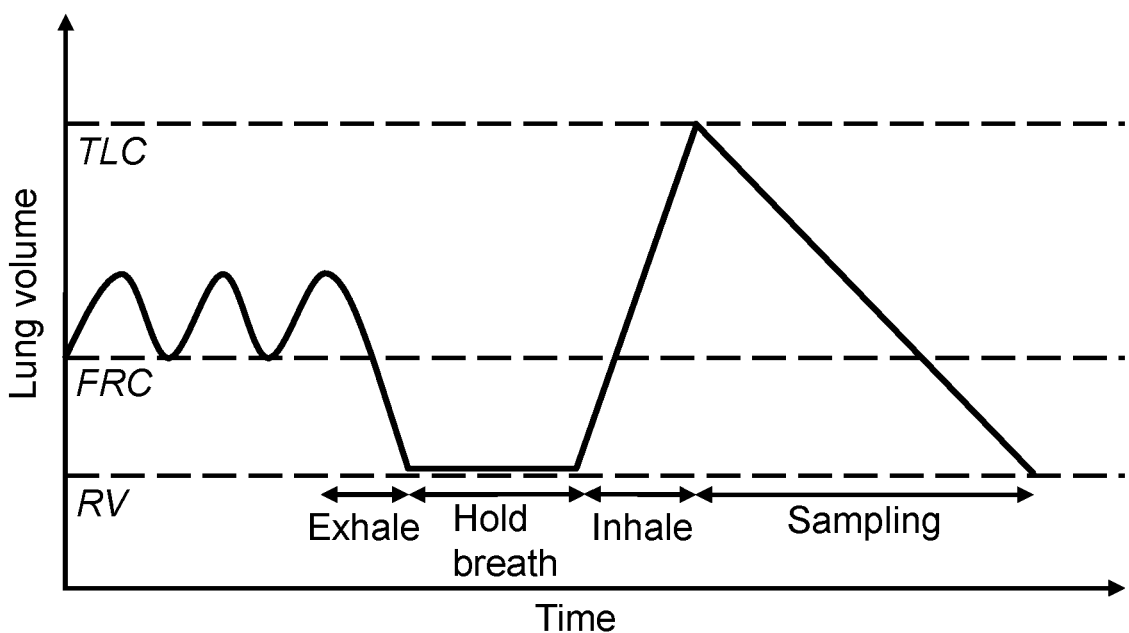

Referring now to FIG. 14, there is shown a graph of the lung volume versus time during an exemplary breathing maneuver according to the present invention. The left part of the graph shows tidal breathing of the user oscillating above the functional residual capacity (FRC) of the lungs, which is the volume in the lungs at the end-expiratory position. After a few breaths, the lung volume then decreases towards residual volume (RV) during deep or maximal exhalation. Thereafter, the lung volume remains constant at residual volume during holding of the breath. Subsequently, the lung volume increases rapidly during maximal inhalation, before decreasing more slowly towards residual volume again during exhalation for sampling.

Preferred embodiments of a portable sampling device for collecting particles, a stand for such a portable sampling device and a tool, as well as a method for collecting aerosol particles in exhaled breath of a user using a portable handheld sampling device according to the invention have been described. However, the person skilled in the art realizes that this can be varied within the scope of the appended claims without departing from the inventive idea.

All the described alternative embodiments above or parts of an embodiment can be freely combined without departing from the inventive idea as long as the combination is not contradictory.

The invention claimed is:

1. A portable handheld sampling device for collecting aerosol particles in a stream of exhaled breath provided with an inlet and an outlet, comprising a housing and a collecting device holder removably arranged at least partially inside the housing, wherein the housing and the collecting device holder are arranged to guide the stream of exhaled breath through the device from the inlet to the outlet, wherein said collecting device holder comprises at least two cylindrical conduits arranged in parallel, each defining a flow path in fluid connection with the inlet, wherein a cylindrical collecting device is arranged in each conduit, each cylindrical collecting device being adapted to collect the aerosol particles in the exhaled breath.

2. The sampling device according to claim 1, wherein each cylindrical collecting device is movably arranged in the collecting device holder such that the each cylindrical collecting device may be removed from the collecting device holder only when the collecting device holder is separated from the housing.

3. The sampling device according to claim 2, wherein each cylindrical collecting device is movably arranged in a direction parallel to the flow path in the collecting device holder.

4. The sampling device according to claim 3, further comprising means for retaining each cylindrical collecting device in an upstream direction in the flow path of the collecting device holder.

5. The sampling device according to claim 4, wherein the retaining means comprises an inwardly directed flange at a distal end of the flow path.

6. The sampling device according to claim 1, wherein the housing comprises an abutment member adapted to abut against a distal end of the cylindrical collecting device when the collecting device holder is arranged inside the housing.

7. The sampling device according to claim 1, further comprising corresponding locking means arranged on the housing and the collecting device holder, respectively.

8. The sampling device according to claim 7, wherein the locking means comprises a cantilever snap-fit connection including at least one deflectable tab comprising a recess arranged on the housing and at least one cantilevered protrusion arranged on the holder, wherein the at least one protrusion is adapted to mate with and engage the recess in the at least one deflectable tab when the housing and the holder are brought together.

9. The sampling device according to claim 1, further comprising at least one lid arranged to cover the inlet and/or the outlet of the sampling device.

10. The sampling device according to claim 1, further comprising a device arranged to measure volume and/or flow of exhaled breath connected in fluid communication with the outlet.

11. The sampling device according to claim 1, wherein the sampling device is disposable.

12. The sampling device according to claim 11, wherein the sampling device is made from a medically acceptable plastic material chosen from polypropylene (PP), polyvinylidene fluoride (PVDF), fluorinated ethylene propylene (FEP) and/or polytetrafluoroethylene (PTFE).

13. A method for collecting aerosol particles in exhaled breath of a user using a portable handheld sampling device provided with an inlet and an outlet, wherein the sampling device further comprises a housing and a collecting device holder removably arranged at least partially inside the housing, wherein the housing and the collecting device holder are arranged to guide the stream of exhaled breath through the device from the inlet to the outlet, wherein said collecting device holder comprises at least two cylindrical conduits arranged in parallel, each conduit defining a flow path in fluid connection with the inlet, wherein a cylindrical collecting device is arranged in each conduit, each cylindrical collecting device being adapted to collect the aerosol particles in the exhaled breath, the method comprising the following steps to be performed by the user:
exhaling deeply to residual volume;
holding breath during a first predetermined period of time;
inhaling deeply to total lung capacity;
placing the portable handheld sampling device at the mouth of the user; and
exhaling through the inlet of the portable handheld sampling device from total lung capacity to residual volume during a second predetermined period of time.

14. The method according to claim 13, wherein the steps to be performed by the user are displayed on a displaying device.

15. The method according to claim 14, wherein the steps are displayed using written, audible and/or graphical instructions.

16. The method according to claim 14, further comprising displaying a timer on the displaying device to indicate the first and/or second predetermined period of time.

17. The method according to claim 13, further comprising connecting a device arranged to measure volume and/or flow of exhaled breath in fluid communication with the outlet of the sampling device prior to the user exhaling through the sampling device.

* * * * *